United States Patent [19]
Fischer, deceased et al.

[11] 4,219,494
[45] Aug. 26, 1980

[54] O-AMINOSULFONYLGLYCOLIC ANILIDES

[75] Inventors: Adolf Fischer, deceased, late of Mutterstadt, Fed. Rep. of Germany, by Caecilia Emma Fischer, heiress-at-law; Hanspeter Hansen, Ludwigshafen, Fed. Rep. of Germany; Wolfgang Rohr; Gerhard Hamprecht, both of Mannheim, Fed. Rep. of Germany

[73] Assignee: BASF Aktiengesellschaft, Fed. Rep. of Germany

[21] Appl. No.: 14,894

[22] Filed: Feb. 23, 1979

Related U.S. Application Data

[63] Continuation of Ser. No. 560,310, Mar. 20, 1975, abandoned.

[30] Foreign Application Priority Data

Apr. 11, 1974 [DE] Fed. Rep. of Germany ....... 2417764

[51] Int. Cl.² ........................................... C07C 143/68
[52] U.S. Cl. ........................... 260/456 A; 260/562 A; 560/250; 71/103
[58] Field of Search ................................... 260/456 A

[56] References Cited

U.S. PATENT DOCUMENTS

| | | | |
|---|---|---|---|
| 3,536,721 | 10/1970 | Soong et al. | 260/456 A |
| 3,849,467 | 11/1974 | Mangold et al. | 260/456 A |
| 3,865,860 | 2/1975 | Rohr et al. | 260/456 A |
| 3,870,740 | 3/1975 | Fischer et al. | 260/456 A |
| 3,898,262 | 8/1975 | Fischer et al. | 260/456 A |

*Primary Examiner*—Nicky Chan
*Attorney, Agent, or Firm*—Keil & Witherspoon

[57] ABSTRACT

New and valuable O-aminosulfonylglycolic anilides, a process for their manufacture, herbicides containing these compounds as active ingredients and a process for controlling the growth of unwanted plants with these compounds.

16 Claims, No Drawings

O-AMINOSULFONYLGLYCOLIC ANILIDES

This is a continuation, of application Ser. No. 560,310, filed Mar. 20, 1975, now abandoned.

This application discloses and claims subject matter described in German patent application No. P 24 17 764.8, filed Apr. 11, 1974, which is incorporated herein by reference.

The present invention relates to new and valuable O-aminosulfonylglycolic anilides, their manufacture and use as herbicides, and herbicides containing these compounds.

It is known (German Laid-Open Application No. DOS 1,543,751) to use chloroacetic acid-N-methoxymethyl-2,6-diethylanilide as a herbicide. However, its herbicidal action is poor.

We have now found that O-aminosulfonylglycolic anilides of the formula

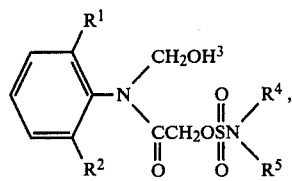

where $R^1$ and $R^2$ each denote $C_1$ to $C_4$ alkyl, $R^3$ denotes $C_1$ to $C_6$ alkyl, alkoxyalkyl, haloalkyl, alkenyl, haloalkenyl, alkynyl, cycloalkyl or heterocycloalkyl, and $R^4$ and $R^5$ each denote hydrogen, alkyl, haloalkyl, cycloalkyl, alkenyl, haloalkenyl, alkynyl or aralkyl, have a good herbicidal action.

$R^1$ and $R^2$ may for instance be methyl, ethyl, propyl, isopropyl, butyl, isobutyl, sec-butyl and tert-butyl.

$R^3$ may for example be methyl, ethyl, propyl, isopropyl, butyl, isobutyl, sec-butyl, tert-butyl, linear or branched amyl and hexyl, 2-chloroethyl, 2,2,2-trifluoroethyl, 1,3-dichloroisopropyl, 1,3-dibromoisopropyl, methoxyethyl, methoxyethoxyethyl, allyl, propargyl, butyn-1-yl-3, 3-methylbutyn-1-yl-3 and cyclopentyl.

Examples of $R^4$ and $R^5$ are hydrogen, methyl, chloromethyl, ethyl, 2-chloroethyl, propyl, isopropyl, butyl, isobutyl, sec-butyl, tert-butyl, pentyl, cyclopentyl, hexyl, cyclohexyl, benzyl, allyl, butenyl, hexenyl, propargyl, butyn-1-yl-3, 3-methylbutyn-1-yl-3, 2-fluoro-2-methylpropyl and 2-fluoropropyl.

The agents have a strong herbicidal action on most shallow-germinating seed and grass weeds.

The new compounds may be prepared in accordance with the following general equation:

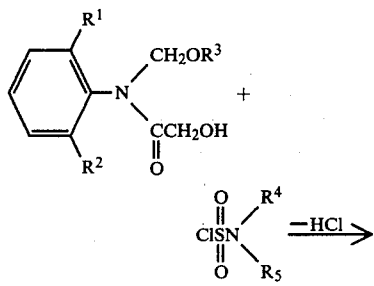

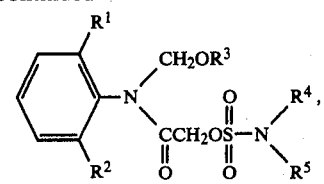

$R^1$, $R^2$, $R^3$, $R^4$ and $R^5$ having the above meanings. The reaction is preferably carried out in the presence of an acid-binding agent.

If a dialkylaminosulfonyl halide is used, it is advisable to employ the appropriate glycolic anilide as a metal salt, preferably an alkali metal salt.

The glycolic anilides required for the reaction may be prepared for instance by the following reactions:

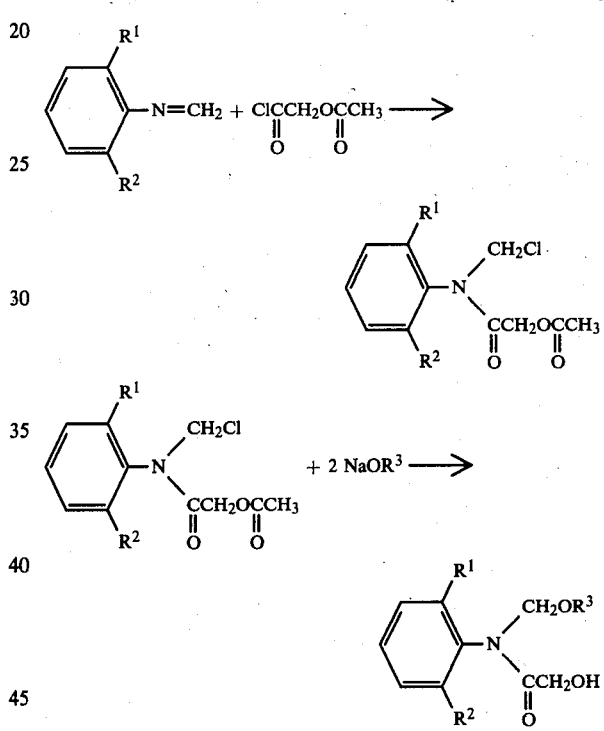

$R^1$, $R^2$ and $R^3$ having the above meanings.

Etherification to the alkoxymethyl group and elimination of the acetyl group may also be carried out stepwise.

EXAMPLE 1

(a) At 0° C. and while stirring, 161 parts (by weight) of N-methylene-2,6-diethylaniline was added to a solution of 136.5 parts of acetoxyacetyl chloride in 150 parts of (dry) ether. To complete the reaction the mixture was stirred for 2 hours at 25° C. The small amount of undissolved material was then removed and the clear solution concentrated in vacuo. 250 parts of ligroin was added and the mixture cooled with ice water, after which the crystalline product was suction filtered; m.p.: 51° to 54° C. After recrystallization from a mixture of ether and ligroin the analytically pure product melted at 56° to 58° C.

The compound has the following structural formula:

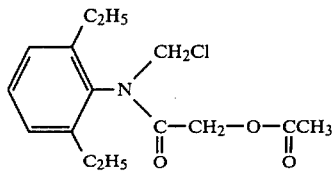

The following compounds were prepared analogously:

| | m.p. °C |
|---|---|
| N-chloromethyl-2,6-dimethyl-O-acetylglycolic anilide | 90–91 |
| N-chloromethyl-2-methyl-6-ethyl-O-acetylglycolic anilide | |
| N-chloromethyl-2,6-diisopropyl-O-acetylglycolic anilide | 148–149 |
| N-chloromethyl-2-methyl-6-isopropyl-O-acetylglycolic anilide | |

(b) At 15° to 20° C. and while stirring, 131 parts (by weight) of a 33 wt% solution of sodium methylate in methanol (additionally diluted with 100 parts of methanol) was added to a solution of 119 parts of N-chloromethyl-2,6-diethyl-O-acetylglycolic anilide in 400 parts of methanol. To complete the reaction the solution was stirred for 15 hours at room temperature. The mixture was then neutralized and concentrated in vacuo. The residue was dissolved with ethyl acetate and washed twice with water.

The organic solution was dried with magnesium sulfate and concentrated in vacuo.

The sirupy residue was purified by distillation; b.p. (0.05 mm) 120° to 125° C., $n_D^{25} = 1.5255$. The compound has the following structural formula:

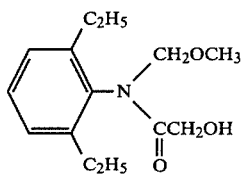

The following compounds were prepared analogously:
N-ethoxymethylglycolic acid-2,6-diethylanilide, b.p.(0.01) 136° to 141° C., $n_D^{25} = 1.5176$
N-propoxymethylglycolic acid-2,6-diethylanilide,
N-isopropoxymethylglycolic acid-2,6-diethylanilide, b.p.(0.01) 125° to 134° C., $n_D^{25} = 1.5146$
N-butoxymethylglycolic acid-2,6-diethylanilide, b.p.(0.01) 147° to 154° C., $n_D^{25} = 1.5112$
N-isobutoxymethylglycolic acid-2,6-diethylanilide,
N-sec-butoxymethylglycolic acid-2,6-diethylanilide,
N-allyloxymethylglycolic acid-2,6-diethylanilide, b.p.(0.1) 132° to 137° C., $n_D^{25} = 1.5267$
N-propargyloxymethylglycolic acid-2,6-diethylanilide, b.p.(0.05) 144° to 148° C., $n_D^{25} = 1.5360$
N-methoxymethylglycolic acid-2,6-dimethylanilide,
N-ethoxymethylglycolic acid-2,6-dimethylanilide, m.p. 47° to 48° C.
N-propoxymethylglycolic acid-2,6-dimethylanilide, b.p.(0.1) 139° to 142° C., $n_D^{25} = 1.5185$
N-isopropoxymethylglycolic acid-2,6-dimethylanilide, b.p.(0.1) 128° to 130° C., $n_D^{25} = 1.5163$
N-butoxymethylglycolic acid-2,6-dimethylanilide,
N-cyclopentyloxymethylglycolic acid-2,6-dimethylanilide,
N-propargyloxymethylglycolic acid-2,6-dimethylanilide b.p.(0.1) 143°–146° C., $n_D^{24} = 1.5422$
N-allyloxymethylglycolic acid-2,6-dimethylanilide, b.p.(0.1) 133°–135° C., $n_D^{20} = 1.5331$
N-isobutoxymethylglycolic acid-2,6-dimethylanilide, b.p.(0.25) 139°–142° C.
N-sec.-butoxymethylglycolic acid-2,6-dimethylanilide, b.p.(1) 160°–165° C.
N-(2,2,2-trifluoroethoxymethylglycolic acid-2,6-dimethylanilide, m.p. 48°–49° C.
N-methoxyethoxymethylglycolic acid-2,6-dimethylanilide,
N-2-chloroethoxymethylglycolic acid-2,6-dimethylanilide,
N-butyn-1-yl-3-oxymethylglycolic acid-2,6-dimethylanilide,
N-methoxymethylglycolic acid-2-methyl-6-ethylanilide,
N-ethoxymethylglycolic acid-2-methyl-6-ethylanilide,
N-propoxymethylglycolic acid-2-methyl-6-ethylanilide,
N-isopropoxymethylglycolic acid-2-methyl-6-ethylanilide,
N-butoxymethylglycolic acid-2-methyl-6-ethylanilide,
N-isobutoxymethylglycolic acid-2-methyl-6-ethylanilide,
N-sec-butoxymethylglycolic acid-2-methyl-6-ethylanilide,
N-allyloxymethylglycolic acid-2-methyl-6-ethylanilide,
N-methoxymethylglycolic acid-2,6-diisopropylanilide, m.p. 124° to 126° C.
N-ethoxymethylglycolic acid-2,6-diisopropylanilide,
N-propoxymethylglycolic acid-2,6-diisopropylanilide,
N-isopropoxymethylglycolic acid-2,6-diisopropylanilide,
N-butoxymethylglycolic acid-2,6-diisopropylanilide,
N-isobutoxymethylglycolic acid-2,6-diisopropylanilide,
N-sec-butoxymethylglycolic acid-2,6-diisopropylanilide,
N-allyloxymethylglycolic acid-2,6-diisopropylanilide,
N-propargyloxymethylglycolic acid-2,6-diisopropylanilide.

(c) N-methoxymethyl-O-methylaminosulfonylglycolic acid-2,6-dimethylanilide

At 0° to −5° C., there were added simultaneously from two supply vessels 17.5 parts by weight of triethylamine and 22.5 parts by weight of methylaminosulfonyl chloride (90%) to a solution of 22.3 parts by weight of N-methoxymethylglycolic acid-2,6-dimethylanilide in 135 parts by weight of dichloromethane. One hour after completion of the additions the reaction mixture was treated with water, dilute hydrochloric acid, water and dilute sodium bicarbonate solution. Drying was effected with magnesium sulfate, followed by concentration of most of the organic phase in vacuo. Ether was added to the residue, and crystallization initiated by trituration and cooling. After some time the crystalline slurry was suction filtered; m.p.: 101° to 102° C.

The compound has the following structural formula:

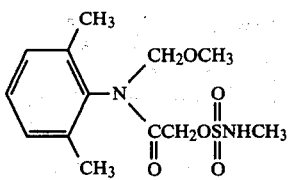

The following compounds were obtained analogously:

N-methoxymethyl-O-ethylaminosulfonylglycolic acid-2,6-dimethylanilide, $n_D^{25}=1.5163$
N-methoxymethyl-O-propylaminosulfonylglycolic acid-2,6-dimethylanilide,
N-methoxymethyl-O-isopropylaminosulfonylglycolic acid-2,6-dimethylanilide,
N-methoxymethyl-O-2-chloroethylaminosulfonylglycolic acid-2,6-dimethylanilide,
N-methoxymethyl-O-2-fluoropropylaminosulfonylglycolic acid-2,6-dimethylanilide,
N-ethoxymethyl-O-methylaminosulfonylglycolic acid-2,6-dimethylanilide, m.p. 84° to 86° C.
N-ethoxymethyl-O-ethylaminosulfonylglycolic acid-2,6-dimethylanilide, m.p. 79° to 80° C.
N-ethoxymethyl-O-propylaminosulfonylglycolic acid-2,6-dimethylanilide,
N-ethoxymethyl-O-isopropylaminosulfonylglycolic acid-2,6-dimethylanilide,
N-ethoxymethyl-O-butylaminosulfonylglycolic acid-2,6-dimethylanilide,
N-ethoxymethyl-O-sec-butylaminosulfonylglycolic acid-2,6-dimethylanilide,
N-ethoxymethyl-O-2-chloroethylaminosulfonylglycolic acid-2,6-dimethylanilide
N-ethoxymethyl-O-2-fluoropropylaminosulfonylglycolic acid-2,6-dimethylanilide
N-propoxymethyl-O-aminosulfonylglycolic acid-2,6-dimethylanilide
N-propoxymethyl-O-methylaminosulfonylglycolic acid-2,6-dimethylanilide, m.p. 48° to 49° C.
N-propoxymethyl-O-ethylaminosulfonylglycolic acid-2,6-dimethylanilide, m.p. 64° to 66° C.
N-propoxymethyl-O-propylaminosulfonylglycolic acid-2,6-dimethylanilide,
N-propoxymethyl-O-isopropylaminosulfonylglycolic acid-2,6-dimethylanilide, m.p. 54° to 56° C.
N-propoxymethyl-O-butylaminosulfonylglycolic acid-2,6-dimethylanilide,
N-propoxymethyl-O-sec-butylaminosulfonylglycolic acid-2,6-dimethylanilide,
N-propoxymethyl-O-2-chloroethylaminosulfonylglycolic acid-2,6-dimethylanilide,
N-propoxymethyl-O-2-fluoropropylaminosulfonylglycolic acid-2,6-dimethylanilide,
N-isopropoxymethyl-O-aminosulfonylglycolic acid-2,6-dimethylanilide,
N-isopropoxymethyl-O-methylaminosulfonylglycolic acid-2,6-dimethylanilide, m.p. 76° to 78° C.
N-isopropoxymethyl-O-ethylaminosulfonylglycolic acid-2,6-dimethylanilide, m.p. 73° to 74° C.
N-isopropoxymethyl-O-propylaminosulfonylglycolic acid-2,6-dimethylanilide,
N-isopropoxymethyl-O-isopropylaminosulfonylglycolic acid-2,6-dimethylanilide, m.p. 80° to 81° C.
N-isopropoxymethyl-O-butylaminosulfonylglycolic acid-2,6-dimethylanilide,
N-isopropoxymethyl-O-sec-butylaminosulfonylglycolic acid-2,6-dimethylanilide,
N-isopropoxymethyl-O-2-chloroethylaminosulfonylglycolic acid-2,6-dimethylanilide
N-isopropoxymethyl-O-2-fluoropropylaminosulfonylglycolic acid-2,6-dimethylanilide
N-butoxymethyl-O-methylaminosulfonylglycolic acid-2,6-dimethylanilide,
N-butoxymethyl-O-ethylaminosulfonylglycolic acid-2,6-dimethylanilide,
N-butoxymethyl-O-propylaminosulfonylglycolic acid-2,6-dimethylanilide,
N-butoxymethyl-O-isopropylaminosulfonylglycolic acid-2,6-dimethylanilide,
N-butoxymethyl-O-butylaminosulfonylglycolic acid-2,6-dimethylanilide,
N-butoxymethyl-O-sec-butylaminosulfonylglycolic acid-2,6-dimethylanilide,
N-butoxymethyl-O-2-chloroethylaminosulfonylglycolic acid-2,6-dimethylanilide,
N-butoxymethyl-O-2-fluoropropylaminosulfonylglycolic acid-2,6-dimethylanilide,
N-isobutoxymethyl-O-methylaminosulfonylglycolic acid-2,6-dimethylanilide,
N-isobutoxymethyl-O-ethylaminosulfonylglycolic acid-2,6-dimethylanilide,
N-isobutoxymethyl-O-propylaminosulfonylglycolic acid-2,6-dimethylanilide,
N-isobutoxymethyl-O-isopropylaminosulfonylglycolic acid-2,6-dimethylanilide,
N-isobutoxymethyl-O-2-chloroethylaminosulfonylglycolic acid-2,6-dimethylanilide,
N-sec-butoxymethyl-O-butylaminosulfonylglycolic acid-2,6-dimethylanilide,
N-sec-butoxymethyl-O-2-chloroethylaminosulfonylglycolic acid-2,6-dimethylanilide,
N-allyloxymethyl-O-ethylaminosulfonylglycolic acid-2,6-dimethylanilide,
N-allyloxymethyl-O-propylaminosulfonylglycolic acid-2,6-dimethylanilide,
N-isobutoxymethyl-O-methylaminosulfonylglycolic acid-2,6-dimethylanilide, m.p. 78°–79° C.
N-sec-butoxymethyl-O-methylaminosulfonylglycolic acid-2,6-dimethylanilide, $n_D^{25}$ 1.5120
N-sec-butoxymethyl-O-ethylaminosulfonylglycolic acid-2,6-dimethylanilide, m.p. 58°–59° C.
N-sec-butoxymethyl-O-propylaminosulfonylglycolic acid-2,6-dimethylanilide, m.p. 75°–76° C.
N-sec-butoxymethyl-O-isopropylaminosulfonylglycolic acid-2,6-dimethylanilide, m.p. 60°–61° C.
N-allyloxymethyl-O-methylaminosulfonylglycolic acid-2,6-dimethylanilide, m.p. 52°–53° C.
N-allyloxymethyl-O-isopropylaminosulfonylglycolic acid-2,6-dimethylanilide,
N-allyloxymethyl-O-butylaminosulfonylglycolic acid-2,6-dimethylanilide,
N-allyloxymethyl-O-sec-butylaminosulfonylglycolic acid-2,6-dimethylanilide,
N-allyloxymethyl-O-2-chloroethylaminosulfonylglycolic acid-2,6-dimethylanilide,
N-allyloxymethyl-O-2-fluoro-2-methylpropylaminosulfonylglycolic acid-2,6-dimethylanilide,
N-propargyloxymethyl-O-methylaminosulfonylglycolic acid-2,6-dimethylanilide, m.p. 71°–73° C.
N-propargyloxymethyl-O-ethylaminosulfonylglycolic acid-2,6-dimethylanilide,
N-propargyloxymethyl-O-propylaminosulfonylglycolic acid-2,6-dimethylanilide, N-propargyloxymethyl-O-isopropylaminosulfonylglycolic acid-2,6-dimethylanilide,
N-propargyloxymethyl-O-butylaminosulfonylglycolic acid-2,6-dimethylanilide,
N-propargyloxymethyl-O-sec-butylaminosulfonylglycolic acid-2,6-dimethylanilide,
N-propargyloxymethyl-O-2-chloroethylaminosulfonylglycolic acid-2,6-dimethylanilide,
N-(2,2,2-trifluoroethoxymethyl)-O-methylaminosulfonylglycolic acid-2,6-dimethylanilide, m.p. 86°–87° C.
N-(2,2,2-trifluoroethoxymethyl)-O-ethylaminosulfonylglycolic acid-2,6-dimethylanilide, m.p. 60°–62° C.

The following compounds were also prepared by this process:

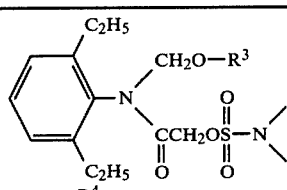

| $R^3$ | $R^4$ | m.p. (°C.) |
|---|---|---|
| CH₃ | H | |
| CH₃ | CH₃ | 74 to 76 |
| CH₃ | C₂H₅ | $n_D^{25}$ = 1.5150 |
| CH₃ | C₃H₇ | |
| CH₃ | i-C₃H₇ | 77 to 79 |
| CH₃ | C₄H₉ | |
| CH₃ | sec-C₄H₉ | |
| CH₃ | CH₂CH₂Cl | 72 to 73 |
| CH₃ | CH₂CF(CH₃)CH₃ | |
| C₂H₅ | H | |
| C₂H₅ | CH₃ | |
| C₂H₅ | C₂H₅ | |
| C₂H₅ | C₃H₇ | |
| C₂H₅ | i-C₃H₇ | 60 to 61 |
| C₂H₅ | C₄H₉ | |
| C₂H₅ | sec-C₄H₉ | |
| C₂H₅ | CH₂CH₂Cl | |
| C₂H₅ | CH₂CF(CH₃)CH₃ | |
| C₃H₇ | H | |
| C₃H₇ | CH₃ | |
| C₃H₇ | C₂H₅ | |
| C₃H₇ | C₃H₇ | |
| C₃H₇ | i-C₃H₇ | |
| C₃H₇ | C₄H₉ | |
| C₃H₇ | sec-C₄H₉ | |
| C₃H₇ | CH₂CH₂Cl | |
| C₃H₇ | CH₂CF(CH₃)CH₃ | |
| i-C₃H₇ | H | |
| i-C₃H₇ | CH₃ | |
| i-C₃H₇ | C₂H₅ | |
| i-C₃H₇ | C₃H₇ | |
| i-C₃H₇ | i-C₃H₇ | |
| i-C₃H₇ | C₄H₉ | |
| i-C₃H₇ | sec-C₄H₉ | |
| i-C₃H₇ | CH₂CH₂Cl | |
| i-C₃H₇ | CH₂CF(CH₃)CH₃ | |
| CH₂CH=CH₂ | H | |
| CH₂CH=CH₂ | CH₃ | $n_D^{25}$ 1.5185 |
| CH₂CH=CH₂ | C₂H₅ | $n_D^{25}$ 1.5160 |
| CH₂CH=CH₂ | C₃H₇ | |
| CH₂CH=CH₂ | i-C₃H₇ | 47–48 |
| CH₂CH=CH₂ | C₄H₉ | |
| CH₂CH=CH₂ | sec-C₄H₉ | |
| CH₂CH=CH₂ | CH₂CH₂Cl | |
| CH₂C≡CH | H | |
| CH₂C≡CH | CH₃ | |
| CH₂C≡CH | C₂H₅ | |
| CH₂C≡CH | C₃H₇ | |
| CH₂C≡CH | i-C₃H₇ | |
| CH₂C≡CH | C₄H₉ | |
| CH₂C≡CH | sec-C₄H₉ | |
| CH₂C≡CH | CH₂CH₂Cl | |

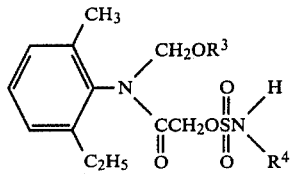

| $R^3$ | $R^4$ | |
|---|---|---|
| CH₃ | H | |
| CH₃ | CH₃ | |
| CH₃ | C₂H₅ | |
| CH₃ | C₃H₇ | |
| CH₃ | i-C₃H₇ | |
| CH₃ | C₄H₉ | |
| CH₃ | sec-C₄H₉ | |
| CH₃ | CH₂CH₂Cl | |
| C₂H₅ | H | |
| C₂H₅ | CH₃ | m.p. 62°–63° C. |
| C₂H₅ | C₂H₅ | $n_D^{25}$ 1.5120 |
| C₂H₅ | i-C₃H₇ | |
| C₂H₅ | C₄H₉ | |
| C₂H₅ | sec-C₄H₉ | |
| C₂H₅ | CH₂CH₂Cl | |
| C₃H₇ | H | |
| C₃H₇ | CH₃ | |
| C₃H₇ | C₂H₅ | |
| C₃H₇ | C₃H₇ | |
| C₃H₇ | i-C₃H₇ | |
| C₃H₇ | C₄H₉ | |
| C₃H₇ | sec-C₄H₉ | |
| C₃H₇ | CH₂CH₂Cl | |
| i-C₃H₇ | H | |
| i-C₃H₇ | CH₃ | |
| i-C₃H₇ | C₂H₅ | |
| i-C₃H₇ | C₃H₇ | |
| i-C₃H₇ | i-C₃H₇ | |
| i-C₃H₇ | C₄H₉ | |
| i-C₃H₇ | sec-C₄H₉ | |
| i-C₃H₇ | CH₂CH₂Cl | |
| CH₂CH=CH₂ | H | |
| CH₂CH=CH₂ | CH₃ | |
| CH₂CH=CH₂ | C₂H₅ | |
| CH₂CH=CH₂ | C₃H₇ | |
| CH₂CH=CH₂ | i-C₃H₇ | |
| CH₂CH=CH₂ | C₄H₉ | |
| CH₂CH=CH₂ | sec-C₄H₉ | |
| CH₂CH=CH₂ | CH₂CH₂Cl | |
| CH₂C≡CH | H | |
| CH₂C≡CH | CH₃ | |
| CH₂C≡CH | C₂H₅ | |
| CH₂C≡CH | C₃H₇ | |
| CH₂C≡CH | i-C₃H₇ | |
| CH₂C≡CH | C₄H₉ | |
| CH₂C≡CH | sec-C₄H₉ | |
| CH₂C≡CH | CH₂CH₂Cl | |

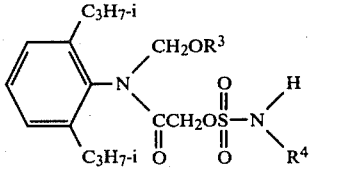

| $R^3$ | $R^4$ | m.p. (°C.) |
|---|---|---|
| CH₃ | H | |
| CH₃ | CH₃ | 83 to 85 |
| CH₃ | C₂H₅ | |
| CH₃ | C₃H₇ | |
| CH₃ | i-C₃H₇ | 90 to 91 |
| CH₃ | C₄H₉ | |
| CH₃ | sec-C₄H₉ | |
| CH₃ | CH₂CH₂Cl | |
| C₂H₅ | H | |
| C₂H₅ | CH₃ | |
| C₂H₅ | C₂H₅ | |
| C₂H₅ | C₃H₇ | |
| C₂H₅ | i-C₃H₇ | |
| C₂H₅ | C₄H₉ | |
| C₂H₅ | sec-C₄H₉ | |
| C₂H₅ | CH₂CH₂Cl | |

-continued

| | |
|---|---|
| C3H7 | H |
| C3H7 | CH3 |
| C3H7 | C2H5 |
| C3H7 | C3H7 |
| C3H7 | i-C3H7 |
| C3H7 | C4H9 |
| C3H7 | sec-C4H9 |
| C3H7 | CH2CH2Cl |
| i-C3H7 | H |
| i-C3H7 | CH3 |
| i-C3H7 | C2H5 |
| i-C3H7 | C3H7 |
| i-C3H7 | i-C3H7 |
| i-C3H7 | C4H9 |
| i-C3H7 | sec-C4H9 |
| i-C3H7 | CH2CH2Cl |

EXAMPLE 2

N-methoxymethyl-O-dimethylaminosulfonylglycolic acid-2,6-diethylanilide

At 20° to 30° C. and while stirring, a solution of 37.7 parts by weight of N-methoxymethylglycolic acid-2,6-diethylanilide was added, according to the rate at which hydrogen evolved, to a suspension of 3.6 parts by weight of sodium hydride in 100 parts by weight of tetrahydrofuran. To complete the reaction the mixture was stirred for 10 hours at 40° C. Subsequently, a solution of 21.6 parts by weight of dimethylaminosulfonyl chloride in 30 parts by weight of tetrahydrofuran was metered, at 15° to 20° C., into the reaction mixture. 2 L hours after all had been added the mixture was concentrated in vacuo. The residue was dissolved in ethyl acetate and treated in turn with water, dilute hydrochloric acid and again with water. Drying was effected with magnesium sulfate and the ethyl acetate solution freed from solvent in vacuo. The sirupy residue ($n_D^{25}$:1.5145) did not crystallize even after standing for a fairly long period of time.

The compound has the following structure:

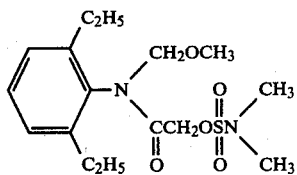

The following compounds were prepared analogously:

| R¹ | R² | R³ | |
|---|---|---|---|
| CH3 | CH3 | CH3 | $n_D^{25}$ 1.5055 |
| CH3 | CH3 | C2H5 | $n_D^{25}$ 1.5083 |
| CH3 | CH3 | C3H7 | |
| CH3 | CH3 | i-C3H7 | |
| CH3 | CH3 | C4H9 | |
| CH3 | CH3 | i-C4H9 | $n_D^{25}$ 1.5030 |
| CH3 | CH3 | CH2CH=CH2 | |
| CH3 | CH3 | CH2C≡CH | |
| C2H5 | C2H5 | CH3 | |

-continued

| R¹ | R² | R³ | R⁴ | R⁵ | $n_D^{25}$ |
|---|---|---|---|---|---|
| C2H5 | C2H5 | C2H5 | | | |
| C2H5 | C2H5 | C3H7 | | | |
| C2H5 | C2H5 | i-C3H7 | | | |
| C2H5 | C2H5 | C4H9 | | | |
| C2H5 | C2H5 | i-C4H9 | | | |
| C2H5 | C2H5 | CH2CH=CH2 | | | |
| C2H5 | C2H5 | CH2C≡CH | | | |
| CH3 | C2H5 | CH3 | | | |
| CH3 | C2H5 | C2H5 | | | $n_D^{25}$ 1.5100 |
| CH3 | C2H5 | C3H7 | | | |
| CH3 | C2H5 | i-C3H7 | | | |
| CH3 | C2H5 | C4H9 | | | |
| CH3 | C2H5 | i-C4H9 | | | |
| CH3 | C2H5 | CH2CH=CH2 | | | |
| CH3 | C2H5 | CH2C≡CH | | | |
| i-C3H7 | i-C3H7 | CH3 | | | |
| i-C3H7 | i-C3H7 | C2H5 | | | |
| i-C3H7 | i-C3H7 | C3H7 | | | |
| i-C3H7 | i-C3H7 | i-C3H7 | | | |
| i-C3H7 | i-C3H7 | C4H9 | | | |
| i-C3H7 | i-C3H7 | sec-C4H9 | | | |
| i-C3H7 | i-C3H7 | CH2CH=CH3 | | | |
| i-C3H7 | i-C3H7 | CH2C≡CH | | | |

| R¹ | R² | R³ | R⁴ | R⁵ | $n_D^{25}$ |
|---|---|---|---|---|---|
| CH3 | CH3 | CH3 | C2H5 | C2H5 | 1.5090 |
| CH3 | CH3 | C2H5 | C2H5 | C2H5 | 1.5100 |
| CH3 | CH3 | C3H7 | C2H5 | C2H5 | |
| CH3 | CH3 | i-C3H7 | C2H7 | C2H5 | |
| C2H5 | C2H5 | CH3 | C2H5 | C2H5 | |
| C2H5 | C2H5 | C2H5 | C2H5 | C2H5 | |
| C2H5 | C2H5 | C3H7 | C2H5 | C2H5 | |
| C2H5 | C2H5 | i-C3H7 | C2H5 | C2H5 | |
| CH3 | C2H5 | CH3 | C2H5 | C2H5 | |
| CH3 | C2H5 | C2H5 | C2H5 | C2H5 | 1.5070 |
| CH3 | C2H5 | C3H7 | C2H5 | C2H5 | |
| CH3 | C2H5 | i-C3H7 | C2H5 | C2H5 | |
| CH3 | CH3 | CH3 | CH3 | C2H5 | |
| CH3 | CH3 | C2H5 | CH3 | C2H5 | |
| CH3 | CH3 | C3H7 | CH3 | C2H5 | |
| CH3 | CH3 | i-C3H7 | CH3 | C2H5 | |
| C2H5 | C2H5 | CH3 | CH3 | C2H5 | |
| C2H5 | C2H5 | CH3 | C2H5 | | |
| C2H5 | C2H5 | C3H7 | CH3 | C2H5 | |
| C2H5 | C2H5 | i-C3H7 | CH3 | C2H5 | |
| CH3 | C2H5 | C2H5 | CH3 | C2H5 | 1.5082 |

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90% by weight of active ingredient.

There may be added to the compositions or individual active ingredients (if desired, immediately before use (tank-mix)) oils of various types, herbicides, fungicides, nematocides, insecticides, bactericides, trace elements, fertilizers, antifoams (e.g., silicones), growth regulators, antidotes and other herbicidally effective compounds such as substituted anilines
substituted aryloxycarboxylic acids and salts, esters and amides thereof,
substituted ethers
substituted arsonic acids and their salts, esters and amides
substituted benzimidazoles
substituted benzisothiazoles
substituted benzothiadiazinone dioxides
substituted benzoxazines
substituted benzoxazinones
substituted benzothiadiazoles
substituted biurets
substituted quinolines
substituted carbamates
substituted aliphatic carboxylic acids and their salts, esters and amides
substituted aromatic carboxylic acids and their salts, esters and amides
substituted carbamoylalkylthiol- or -dithiophosphates
substituted quinazolines
substituted cycloalkylamidocarbothiolic acids and their salts,
esters and amides
substituted cycloalkylcarbonamidothiazoles
substituted dicarboxylic acids and their salts, esters and amides
substituted dihydrobenzofuranyl sulfonates
substituted disulfides
substituted dipyridylium salts
substituted dithiocarbamates
substituted dithiophosphoric acids and their salts, esters and amides
substituted ureas
substituted hexahydro-1H-carbothioates
substituted hydantoins
substituted hydrazides
substituted hydrazonium salts
substituted isoxazole pyrimidones
substituted imidazoles
substituted isothiazole pyrimidones
substituted ketones
substituted naphthoquinones
substituted aliphatic nitriles
substituted aromatic nitriles
substituted oxadiazoles
substituted oxadiazinones
substituted oxadiazolidine diones
substituted oxadiazine diones
substituted phenols and their salts and esters
substituted phosphonic acids and their salts, esters and amides
substituted phosphonium chlorides
substituted phosphonalkyl glycines
substituted phosphites
substituted phosphoric acids and their salts, esters and amides
substituted piperidines
substituted pyrazoles
substituted pyrazole alkylcarboxylic acids and their salts,
esters and amides
substituted pyrazolium salts
substituted pyrazolium alkyl sulfates
substituted pyridazines
substituted pyridazones
substituted pyridine carboxylic acids and their salts,
esters and amides
substituted pyridines
substituted pyridine carboxylates
substituted pyridinones
substituted pyrimidines
substituted pyrimidones
substituted pyrrolidine carboxylic acid and its salts,
esters and amides
substituted pyrrolidines
substituted pyrrolidones
substituted arylsulfonic acids and their salts, esters and amides
substituted styrenes
substituted tetrahydrooxadiazine diones substituted tetrahydroxadiazole diones
substituted tetrahydromethanoindenes
substituted tetrahydroxadiazole thiones
substituted tetrahydrothiadiazine thiones
substituted tetrahydrothiadiazole diones
substituted aromatic thiocarbonylamides
substituted thiocarboxylic acids and their salts, esters and amides
substituted thiol carbamates
substituted thioureas
substituted thiophosphoric acids and their salts, esters and amides
substituted triazines
substituted triazoles
substituted uracils, and
substituted uretidine diones.

The last-mentioned herbicidal compounds may also be applied before or after the active ingredients or compositions thereof according to the invention.

These agents may be added to the herbicides according to the invention in a ratio by weight of from 1:10 to 10:1. The same applies to oils, fungicides, nematocides, insecticides, bactericides, antidotes and growth regulators.

The amount used of the agents according to the invention may vary and depends in essence on the type of effect to be achieved; it is generally from 0.1 to 15 (and more), preferably from 0.2 to 6, kg per hectare of active ingredient. The agents according to the invention may be used once or several times before or after planting, before sowing, and before, during or after emergence of the crop plants and unwanted plants.

The new compositions have a strong herbicidal action and may therefore be used as weedkillers or for controlling the growth of unwanted plants. Whether the new active ingredients are used as total or selective agents depends in essence on the amount of ingredient used per unit area.

By weeds and unwanted plant growth are meant all monocotyledonous and dicotyledonous plants which grow in loci where they are not desired.

The agents according to the invention may therefore be used for controlling for instance Gramineae, such as

| | |
|---|---|
| Cynodon spp. | Dactylis spp. |
| Digitaria spp. | Avena spp. |
| Echinochloa spp. | Bromus spp. |
| Setaria spp. | Uniola spp. |
| Panicum spp. | Poa spp. |
| Alopecurus spp. | Leptochloa spp. |
| Lolium spp. | Brachiaria spp. |
| Sorghum spp. | Eleusine spp. |
| Agropyron spp. | Cenchrus spp. |
| Phalaris spp. | Eragrostis spp. |
| Apera spp. | *Phragmites communis* |
| etc.; | |
| Cyperaceae, such as | |
| Carex spp. | Eleocharis spp. |
| Cyperus spp. | Scirpus spp. |
| etc.; | |
| dicotyledonous weeds, such as | |
| Malvaceae, e.g., | |
| *Abutilon theoprasti* | |
| Sida spp. | Hibiscus spp. |
| etc.; | Malva spp. |
| Compositae, such as | |
| Ambrosia spp. | Centaurea spp. |
| Lactuea spp. | Tussilago spp. |
| Senecio spp. | *Lapsana communis* |
| Sonchus spp. | Tagetes spp. |
| Xanthium spp. | Erigeron spp. |

-continued

| | |
|---|---|
| Iva spp. | Anthemis spp. |
| Galinsoga spp. | Matricaria spp. |
| Taraxacum spp. | Artemisia spp. |
| Chrysanthemum spp. | Bidens spp. |
| Cirsium spp. | etc.; |
| Convolvulaceae, such as | |
| Convolvulus spp. | Cuscuta spp. |
| Ipomoea spp. | *Jaquemontia tamnifolia* |
| etc.; | |
| Cruciferae, such as | |
| *Barbarea vulgaris* | *Arabidopsis thaliana* |
| Brassica spp. | Descurainia spp. |
| Capsella spp. | Draba spp. |
| Sisymbrium spp. | *Coronopus didymus* |
| Thlaspi spp. | Lepidium spp. |
| *Sinapis arvensis* | Raphanus spp. |
| etc.; | |
| Geraniaceae, such as | |
| Erodium spp. | Germanium spp. |
| etc.; | |
| Portulaceceae, such as | |
| Portulaca spp. | etc.; |
| Primulaceae, such as | |
| *Anagallis arvensis* | Lysimachia spp. |
| etc.; | |
| Rubiaceae such as | |
| Richardia spp. | Diodia spp. |
| Galium spp. | etc.; |
| Scrophulariaceae, such as | |
| Linaria spp. | Digitalis spp. |
| Veronica spp. | etc.; |
| Solanaceae, such as | |
| Physalis spp. | Nicandra spp. |
| Solanum spp. | Datura spp. |
| etc.; | |
| Urticaceae, such as | |
| Urtica spp. | |
| Violaceae, such as | |
| Viola spp. | etc.; |
| Zygophyllaceae, such as | |
| *Tribulus terrestris* | etc.; |
| Euphorbiaceae, such as | |
| *Mercurialis annua* | Euphorbia spp. |
| Umbelliferae, such as | |
| *Daucus carota* | *Ammi majus* |
| *Aethusa cynapium* | etc.; |
| Commelinaceae, such as | |
| Commelina spp. | etc.; |
| Labiatae, such as | |
| Lamium spp. | Galeopsis spp. |
| etc.; | |
| Leguminosae, such as | |
| Medicago spp. | *Sesbania exaltata* |
| Trifolium spp. | Cassia spp. |
| Vicia spp. | Lathyrus spp. |
| etc.; | |
| Plantaginaceae, such as | |
| Plantago spp. | etc.; |
| Polygonaceae, such as | |
| Polygonum spp. | Fagopyrum spp. |
| Sumex spp. | etc.; |
| Aizoaceae, such as | |
| *Mollugo verticillata* | etc.; |
| Amaranthaceae, such as | |
| Amaranthus spp. | etc.; |
| Boraginaceae, such as | |
| Amsinckia spp. | Anchusa spp. |
| Myostis spp. | Lithospermum spp. |
| etc.; | |
| Caryophyllaceae, such as | |
| Stellaria spp. | Silene spp. |
| Spergula spp. | Cerastium spp. |
| Saponaria spp. | *Agrostemma githago* |
| *Scleranthus annuus* | etc.; |
| Chenopodiaceae, such as | |
| Chenopodium spp. | Atriplex spp. |
| Kochia spp. | *Monolepsis nuttalliana* |
| Salsola Kali | etc.; |
| Lythraceae, such as | |
| Cuphea spp. | etc.; |
| Oxalidaceae, such as | |
| Oxalis spp. | |

-continued

| Ranunculaceae, such as | |
|---|---|
| Ranunculus spp. | Adonis spp. |
| Delphinium spp. | etc.; |
| Papaveraceae, such as | |
| Papaver spp. | *Fumaria officinalis* |
| etc.; | |
| Onagraceae, such as | |
| Jussiaea spp. | etc.; |
| Rosaceae, such as | |
| Alchemillia spp. | Potentilla spp. |
| etc.; | |
| Potamogetonaceae, such as | |
| Potamogeton spp. | etc.; |
| Najadaceae, such as | |
| Najas spp. | etc.; |
| Equisetaceae | |
| Equisetum spp. | etc.; |
| Marsileaceae, such as | |
| *Marsilea quadrifolia* | etc.; |
| Polypodiaceae, | |
| *Pteridium quilinum* | |
| Alismataceae, such as | |
| Alisma spp. | *Sagittaria sagittifolia* |
| etc. | |

The herbicides according to the invention may be employed in cereal crops such as

| | |
|---|---|
| Avena spp. | Sorghum |
| Triticum spp. | Zea mays |
| Hordeum spp. | *Panicum miliaceum* |
| Secale spp. | Oryza spp. |
| *Saccharum officinarum* | | and in dicotyledon crops such as
Cruciferae, e.g.

| | |
|---|---|
| Brassica spp. | Raphanus spp. |
| Sinapis spp. | Lepidium spp. |
| Compositae, e.g. | |
| Lactuca spp. | Carthamus spp. |
| Helianthus spp. | Scorzonera spp. |
| Malvaceae, e.g. | |
| *Gossypium hirsutum* | |
| Leguminosae, e.g. | |
| Medicago spp. | Phaseolus spp. |
| Trifolium spp. | Arachis spp. |
| Pisum spp. | Glycine max. |
| Chenopodiaceae, e.g. | |
| *Beta vulgaris* | |
| Spinacia spp. | |
| Solanaceae, e.g. | |
| Solanum spp. | *Capsicum annuum* |
| Nicotiania spp. | |
| Linaceae, e.g. | |
| Linum spp. | |
| Umbelliferae, e.g. | |
| Petroselinum spp. | *Apium graveolens* |
| *Daucus carota* | |
| Rosaceae, e.g. | Fragaria |
| Cucurbitaceae, e.g. | |
| Cucumis spp. | Cucurbita spp. |
| Liliaceae, e.g. | |
| Allium spp. | |
| Vitaceae, e.g. | |
| *Vitis vinifern* | |
| Dromeliaceae, e.g. | |
| Ananas sativus. | |

EXAMPLE 3

In the greenhouse, loamy sandy soil was filled into pots and sown with the seeds of various plants. The soil was then immediately treated with 3 kg per hectare of each of the following active ingredients, each being dispersed or emulsified in 500 liters of water per hectare:

I  N-methoxymethyl-O-methylaminosulfonylglycolic acid-2,6-diethylanilide
II  N-methoxymethyl-O-dimethylaminosulfonylglycolic acid-2,6-diethylanilide
III  N-ethoxymethyl-O-isopropylaminosulfonylglycolic acid-2,6-diethylanilide
IV  N-methoxymethyl-O-ethylaminosulfonylglycolic acid-2,6-diethylanilide
V  N-methoxymethyl-O-ethylaminosulfonylglycolic acid-2,6-dimethylanilide
VI  N-ethoxymethyl-O-methylaminosulfonylglycolic acid-2,6-dimethylanilide
VII  N-ethoxymethyl-O-ethylaminosulfonylglycolic acid-2,6-dimethylanilide
VIII  N-propoxymethyl-O-methylaminosulfonylglycolic acid-2,6-dimethylanilide
IX  N-isopropoxymethyl-O-methylaminosulfonylglycolic acid-2,6-dimethylanilide and, for comparison,
X  N-methoxymethylchloroacetic acid-2,6-diethylanilide.

After 4 to 5 weeks it was ascertained that active ingredients I to IX had better compatibility with the crop plants than X, combined with the same herbicidal action.

The results are given below:

| Active ingredient kg/ha | I 3 | II 3 | III 3 | IV 3 | V 3 | VI 3 | VII 3 | VIII 3 | IX 3 | X 3 |
|---|---|---|---|---|---|---|---|---|---|---|
| Crop plants: | | | | | | | | | | |
| *Brassica napus* | 0 | 0 | 0 | 0 | 0 | 0 | 0 | 0 | 0 | 40 |
| *Zea mays* | 0 | 0 | 0 | 0 | 0 | 0 | 0 | 0 | 0 | 5 |
| *Glycine max* | 0 | 0 | 0 | 0 | 0 | 0 | 0 | 0 | 0 | 7 |
| *Gossypium hirsutum* | 0 | 0 | 0 | 0 | 0 | 0 | 0 | 0 | 0 | 10 |
| *Beta vulgaris* | 0 | 10 | 10 | 0 | 5 | 10 | 10 | 0 | 0 | 60 |
| Unwanted plants: | | | | | | | | | | |
| *Lolium multiflorum* | 95 | 100 | 100 | 95 | 100 | 100 | 100 | 100 | 95 | 90 |
| *Poa annua* | 95 | 100 | 100 | 95 | 100 | 100 | 100 | 100 | 100 | 90 |
| *Echinochloa crus-galli* | 95 | 100 | 100 | 100 | 100 | 100 | 100 | 100 | 100 | 95 |

0 = no damage
100 = complete destruction

EXAMPLE 4

In the greenhouse, various plants were treated at a growth height of from 2 to 18 cm with 3 kg per hectare of each active ingredients I to X, each being dispersed or emulsified in 500 liters of water per hectare.

After 2 to 3 weeks it was ascertained that active ingredients I to IX had better compatibility with the crop plants than X, combined with a superior herbicidal action.

The results are given below:

| Active ingredient kg/ha | I 3 | II 3 | III 3 | IV 3 | V 3 | VI 3 | VII 3 | VIII 3 | IX 3 | X 3 |
|---|---|---|---|---|---|---|---|---|---|---|
| Crop plants: | | | | | | | | | | |
| Brassica napus | 5 | 0 | 0 | 0 | 0 | 5 | 5 | 0 | 0 | 30 |
| Beta vulgaris | 0 | 5 | 5 | 5 | 5 | 5 | 5 | 0 | 0 | 20 |
| Unwanted plants: | | | | | | | | | | |
| Lolium multiforum | 75 | 80 | 80 | 75 | 80 | 80 | 75 | 90 | 80 | 45 |
| Poa annua | 75 | 75 | 80 | 75 | 80 | 85 | 80 | 80 | 80 | 50 |
| Echinochloa crus-galli | 75 | 75 | 75 | 75 | 75 | 85 | 80 | 90 | 80 | 40 |
| Sinapis arvensis | 75 | 65 | 70 | 70 | 70 | 75 | 70 | 60 | 60 | 20 |
| Polygonum persicaria | 85 | 75 | 70 | 65 | 70 | 75 | 70 | — | — | 10 |
| Matricaria chamomilla | 80 | 70 | 75 | 70 | 75 | 75 | 70 | — | — | 55 |
| Chenopodium album | 80 | 70 | 80 | 70 | 75 | 70 | 75 | — | — | 55 |

0 = no damage
100 = complete destruction

The action of the following compounds corresponds to that of I to IX in Examples 3 and 4:

N-methoxymethyl-O-isopropylaminosulfonylglycolic acid-2,6-diethylanilide

N-methoxymethyl-O-ethylaminosulfonylglycolic acid-2,6-diisopropylanilide

N-methoxymethyl-O-isopropylaminosulfonylglycolic acid-2,6-diisopropylanilide

N-methoxymethyl-O-methylaminosulfonylglycolic acid-2,6-dimethylanilide

N-n-propoxymethyl-O-ethylaminosulfonylglycolic acid-2,6-dimethylanilide

N-n-propoxymethyl-O-isopropylaminosulfonylglycolic acid-2,6-dimethylanilide

N-isopropoxymethyl-O-ethylaminosulfonylglycolic acid-2,6-dimethylanilide

N-isopropoxymethyl-O-isopropylaminosulfonylglycolic acid-2,6-dimethylanilide

EXAMPLE 5

90 parts by weight of compound I is mixed with 10 parts by weight of N-methyl-α-pyrrolidone. A mixture is obtained which is suitable for application in the form of very fine drops.

EXAMPLE 6

20 parts by weight of compound II is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dedecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 7

20 parts by weight of compound III is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 8

20 parts by weight of compound IV is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 9

20 parts by weight of compound I is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 10

3 parts by weight of compound II is intimately mixed with 97 parts by weight of particulate kaolin. A dust is obtained containing 3% by weight of the active ingredient.

EXAMPLE 11

30 parts by weight of compound III is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 12

In the greenhouse, loamy sandy soil was filled into pots and sown with the seeds of various plants. The soil was then immediately treated with 3 kg per hectare of each of the following active ingredients, each being dispersed or emulsified in 500 liters of water per hectare:

XI  N-ethoxymethyl-O-methylaminosulfonylglycolic acid-2-methyl-6-ethylanilide
XII  N-ethoxymethyl-O-ethylaminosulfonylglycolic acid-2-methyl-6-ethylanilide
XIII  N-ethoxymethyl-O-dimethylaminosulfonylglycolic acid-2-methyl-6-ethylanilide
XIV  N-ethoxymethyl-O-methylethylaminosulfonylglycolic acid-2-methyl-6-ethylanilide
XV  N-ethoxymethyl-O-diethylaminosulfonylglycolic acid-2-methyl-6-ethylanilide
XVI  N-sec-butoxymethyl-O-methylaminosulfonylglycolic acid-2,6-dimethylanilide After 4 to 5 weeks it was ascertained that the active ingredients XI to XVI had good compatibility with the crop plant and a strong herbicidal action.

The results are given below:

| Active ingredient kg/ha | XI 3 | XII 3 | XIII 3 | XIV 3 | XV 3 | XVI 3 |
|---|---|---|---|---|---|---|
| Crop plant: | | | | | | |
| Sinapis alba | 0 | 0 | 0 | 0 | 0 | 0 |

| Active ingredient kg/ha | XI 3 | XII 3 | XIII 3 | XIV 3 | XV 3 | XVI 3 |
|---|---|---|---|---|---|---|
| Unwanted plants | | | | | | |
| *Echinochloa crus-galli* | 95 | 95 | 95 | 100 | 100 | 90 |
| *Lolium multiflorum* | 90 | 90 | 95 | 95 | 100 | 95 |

The following compounds have a similar action:

N-sec-butoxymethyl-O-ethylaminosulfonylglycolic acid-2,6-dimethylanilide

N-sec-butoxymethyl-O-n-propylaminosulfonylglycolic acid-2,6-dimethylanilide

N-sec-butoxymethyl-O-isopropylaminosulfonylglycolic acid-2,6-dimethylanilide

N-isobutoxymethyl-O-methylaminosulfonylglycolic acid-2,6-dimethylanilide

N-isobutoxymethyl-O-dimethylaminosulfonylglycolic acid-2,6-dimethylanilide

We claim:

1. An O-aminosulfonylglycolic anilide of the formula

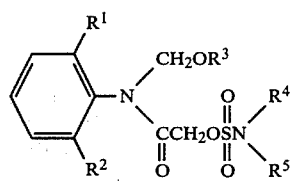

where $R^1$ and $R^2$ each denote alkyl of 1 to 4 carbon atoms, $R^3$ denotes alkyl of 1 to 6 carbon atoms, $R^4$ and $R^5$ respectively denote methyl, ethyl, propyl, isopropyl, butyl, isobutyl, secbutyl, tert-butyl, pentyl or hexyl, and $R^4$ may further denote hydrogen.

2. N-sec-butoxymethyl-O-methylaminosulfonylglycolic acid-2,6-dimethylanilide.

3. N-methoxymethyl-O-ethylaminosulfonylglycolic acid-2,6-dimethylanilide.

4. N-ethoxymethyl-O-methylaminosulfonylglycolic acid-2,6-dimethylanilide.

5. N-ethoxymethyl-O-ethylaminosulfonylglycolic acid-2,6-dimethylanilide.

6. N-propoxymethyl-O-methylaminosulfonylglycolic acid-2,6-dimethylanilide.

7. N-isopropoxymethyl-O-methylaminosulfonylglycolic acid-2,6-dimethylanilide.

8. N-methoxymethyl-O-methylaminosulfonylglycolic acid-2,6-diethylanilide.

9. N-methoxymethyl-O-ethylaminosulfonylglycolic acid-2,6-diethylanilide.

10. N-methoxymethyl-O-isopropylaminosulfonylglycolic acid-2,6-diethylanilide.

11. N-methoxymethyl-O-dimethylaminosulfonylglycolic acid-2,6-diethylanilide.

12. N-ethoxymethyl-O-methylaminosulfonylglycolic acid-2-methyl-6-ethylanilide.

13. N-ethoxymethyl-O-ethylaminosulfonylglycolic acid-2-methyl-6-ethylanilide.

14. N-ethoxymethyl-O-dimethylaminosulfonylglycolic acid-2-methyl-6-ethylanilide.

15. N-ethoxymethyl-O-methyl-ethylaminosulfonylglycolic acid-2-methyl-6-ethylanilide.

16. N-ethoxymethyl-O-diethylaminosulfonylglycolic acid-2-methyl-6-ethylanilide.

* * * * *